United States Patent [19]

Duvel

[11] Patent Number: 5,034,218
[45] Date of Patent: Jul. 23, 1991

[54] STABLE CONDITIONING SHAMPOO CONTAINING COMPATIBLE ANIONIC SURFACTANT/CATIONIC CONDITIONING AGENT-NON-VOLATILE SILICONE EMULSION

[75] Inventor: Lane A. Duvel, River Forest, Ill.

[73] Assignee: Helene Curtis, Inc., Chicago, Ill.

[21] Appl. No.: 552,437

[22] Filed: Jul. 13, 1990

[51] Int. Cl.$^5$ .............................................. A61K 7/075
[52] U.S. Cl. ........................................ 424/70; 424/78; 424/81; 252/547; 252/174.15; 252/174.23; 252/174.24; 252/DIG. 2; 252/DIG. 13
[58] Field of Search ............................ 424/70, 81, 78; 252/DIG. 13, 15, 547, 174.15, 174.23, 174.24, DIG. 2

[56] References Cited

U.S. PATENT DOCUMENTS

| | | | |
|---|---|---|---|
| 2,826,551 | 3/1958 | Geen | 252/DIG. 14 X |
| 3,822,312 | 7/1974 | Sato | 424/70 X |
| 3,849,348 | 11/1974 | Hewitt | 252/DIG. 13 X |
| 3,964,500 | 6/1976 | Drakoff | 424/70 X |
| 3,990,991 | 11/1976 | Gerstein | 434/70 X |
| 4,364,837 | 12/1982 | Pader | 424/70 X |
| 4,704,272 | 11/1987 | Oh et al. | 424/70 |
| 4,741,855 | 5/1988 | Grote et al. | 424/70 X |
| 4,788,006 | 11/1988 | Bolich, Jr. et al. | 252/DIG. 2 |
| 4,830,774 | 5/1989 | LaPetina et al. | 252/174.24 |
| 4,902,499 | 2/1990 | Bolich, Jr. et al. | 252/DIG. 13 |

Primary Examiner—Thurman Page
Attorney, Agent, or Firm—Marshall, O'Toole, Gerstein, Murray & Bicknell

[57] ABSTRACT

A hair conditioning shampoo composition comprising an emulsion of water; about 5 to about 65 percent by weight of an anionic cleaning surfactant, such as ammonium lauryl sulfate; from about 0.1 to about 20 percent by weight of a cationic di-long chain alkyl quaternary nitrogen-containing conditioning agent, wherein the long alkyl chains bonded to the nitrogen atom have from about 12 to about 22 carbon atoms per alkyl chain, such as distearyl dimethyl ammonium chloride; from about 0.5 to about 10 weight percent of a long chain fatty alcohol having about 8 to about 32 carbons in the long chain, such as stearyl alcohol; from about 0.5 to about 10 weight percent of a non-volatile silicone; and about 0.1 to about 5% of an anionic cross-linked polymeric suspending agent, such as polyacrylic acid.

25 Claims, No Drawings

STABLE CONDITIONING SHAMPOO CONTAINING COMPATIBLE ANIONIC SURFACTANT/CATIONIC CONDITIONING AGENT-NON-VOLATILE SILICONE EMULSION

FIELD OF INVENTION

The present invention is directed to a hair conditioning shampoo composition and to a method of treating hair with the composition to cleanse the hair and, at the same time, to provide the hair with unexpectedly improved wet stage and dry stage conditioning properties as well as other conditioning properties, such as softness, without residual build-up of conditioning agents on the hair. More particularly, the present invention is directed to a hair conditioning shampoo composition including one or more anionic cleaning surfactants, such as ammonium lauryl sulfate, one or more non-volatile silicone oils, such as a polydimethylsiloxane compound, a water-insoluble, oil-soluble di-long chain alkyl, quaternary ammonium salt conditioning agent, a long chain fatty alcohol, and an anionic polymeric suspending agent, such as a polyacrylic acid suspending agent. Surprisingly, and contrary to the teachings of the prior art, the anionic surfactant/cationic di-long chain alkyl quaternary ammonium salts are compatible, when combined with an anionic polymeric suspending agent, to effectively suspend the non-volatile silicone oils in the composition without the problem of anionic surfactantcationic conditioning agent incompatibility.

BACKGROUND OF THE INVENTION AND PRIOR ART

Soiled human hair is shampooed to remove sebum that is naturally secreted by the head as well as soil and other atmospheric contaminants that accumulate on the hair. Sebum, in particular, accumulates on the hair in a relatively short period of time leaving the hair with a greasy, dirty feel and poor manageability. The most effective shampoos for cleansing the hair for removal of the atmospheric contaminants and sebum, are those that contain high lather synthetic anionic detergents, such as the long chain alkyl sulfates and the partially ethoxylated long chain alkyl sulfates. These synthetic anionic detergents are very effective for cleansing the hair but, after rinsing with water, leave the hair with a dried touch, usually called "creak" and result in hair, when wet, that is in an extremely tangled and unmanageable after-shampoo condition.

Thoroughly cleansed hair is extremely difficult to comb, in either the wet or dry state because the individual hair fibers tend to snarl, kink, and interlock with each other. Particularly prior to complete drying of thoroughly cleansed hair, in this after-shampoo stage, the hair is very difficult to comb or brush. Even after complete drying, the thoroughly cleansed hair remains difficult to comb or brush and does not set well. Thoroughly clean, dried hair also has undesirable electrostatic properties in a low humidity atmosphere that causes the hair to "fly away", thereby further reducing the combing or brushing property of the hair. Generally, these above-outlined problems that result from synthetic detergent cleansing of the hair, particularly the high-lather synthetic anionic detergents, have been elevated either by the after-shampoo treatment of the hair with hair conditioners, for example in the form of a hair rinse, or by including hair conditioners directly within the shampoo composition.

After-shampoo hair conditioning compositions are easily formulated but are inconvenient to use because of the necessity of applying the conditioner to the hair in a separate stage, after shampooing. The preparation of a conditioning shampoo has been more difficult because of inherent incompatibility problems between anionic surfactants and the fatty cationic compounds that are good conditioning agents. Contact between an anionic surfactant and a cationic surfactant or cationic polymer produces a precipitate that forms immediately or causes an interaction between the anionic and cationic compounds that significantly reduces their respective cleansing and conditioning properties. The reduction in cleansing and conditioning effectiveness is observed even in compositions wherein the anionic and cationic compounds do not precipitate from the composition but remain in solution or suspension. This incompatibility between an anionic surfactant and a cationic conditioning compound is well recognized by those skilled in the art. For example, Sagarin in *Cosmetics*, Interscience Publishers, Inc., New York, p. 538 (1957), states that anionic and cationic compounds cannot be used in combination because they react to form insoluble salts.

A partial solution to this incompatibility problem in the formulation of conditioning shampoos is exemplified by the following patents that disclose compositions that contain surfactants that are not anionic e.g. nonionics, amphoterics and zwitterionics together with cationic conditioning compounds: U.S. Pat. No. 3,849,348 to Hewitt; U.S. Pat. No. 3,990,991 to Gerstein; and U.S. Pat. No. 3,822,312 to Sato.

Another problem inherent in formulating a conditioning shampoo is an instability problem that results when water-insoluble conditioning agents are also included in the conditioning shampoo composition, such as the non-volatile silicones that are well recognized in the art as providing a degree of softness to the hair.

Silicones in shampoo compositions have been disclosed in a number of different patents: U.S. Pat. No. 2,826,551, Mar. 11, 1958 to Green; U.S. Pat. No. 3,964,500, June 22, 1976 to Drakoff; U.S. Pat. No. 4,364,837, Dec. 21, 1982 to Pader; British Pat. No. 849,433, Sept. 28, 1960 to Woolston; U.S. Pat. No. 4,741,855 to Grote, et al.; U.S. Pat. Nos. 4,788,006 and 4,902,499 to Bolich, Jr. et al. and U.S. Pat. No. 4,704,272 to Oh et al.

A particularly difficult problem to solve in silicone-containing conditioning shampoos is that of keeping a dispersed, insoluble, non-volatile silicone material suspended in stable form while retaining the cleansing and conditioning performance of the conditioning shampoo. The stability problem is particularly prevalent in conditioning shampoos like those disclosed herein containing an anionic surfactant and a cationic conditioning material which, as outlined above, by themselves tend to interact and present stability problems. A variety of materials have been proposed for inclusion in silicone-containing conditioning shampoos for purposes of thickening and stabilization such as xanthan gum, long chain acyl derivatives, long chain amide oxides, and long chain alkanolamides as disclosed in U.S. Pat. Nos. 4,788,006; 4,704,272; and 4,741,855.

SUMMARY OF THE INVENTION

In accordance with the principles of the present invention, it has been found, surprisingly, that a conditioning shampoo containing an anionic surfactant, a cationic di-long chain alkyl quaternary ammonium salt, a long chain fatty alcohol, and a non-volatile silicone material has extended product stability, excellent cleansing properties and provides unexpected overall conditioning to human hair, particularly superior wet and dry combing properties when combined with an anionic cross-linked polymeric suspending agent.

Surprisingly and unexpectedly, compositions of the present invention are stable and do not exhibit the inherent anionic surfactant/cationic conditioning agent incompatibility. It was further surprisingly and unexpectedly found that hair treated with the composition of the present invention is thoroughly cleansed and exhibits improved physical and cosmetic properties, such as gloss, thickness, manageability, softness and body. Further, it was surprisingly and unexpectedly found that hair treated with the compositions of the present invention does not experience build-up on the hair shaft, over time, of conditioning agents, as is common with many conditioning shampoo compositions.

Therefore, an aspect of the present invention is to provide a hair-treating composition that cleanses the hair and imparts improved physical properties and cosmetic properties to the hair in a single application.

Another aspect of the present invention is to provide a physically stable conditioning shampoo containing an anionic surfactant, a cationic conditioning agent, and a non-volatile silicone.

Another aspect of the present invention is to provide a new and improved conditioning shampoo containing a strong anionic detergent, such as a long chain alkyl sulfate, long chain alkyl ether sulfate, and/or long chain sulfonate, that is compatible with a cationic quaternary ammonium conditioning agent and a non-volatile silicone conditioning agent, that is unexpectedly stable due to an anionic polymeric suspending agent.

Still another aspect of the present invention is to provide a new and improved conditioning shampoo including about 5% to about 65% of an anionic surfactant; about 0.1% to about 20% of a cationic, nitrogen-containing conditioning agent having only two long chain alkyl radicals bonded to the nitrogen atom, the long chain radicals having predominantly about 12 to about 22 carbon atoms per long chain alkyl radical; about 0.5% to about 10% of a non-volatile silicone material; about 0.5% to about 10% of a long chain fatty alcohol and about 0.1% to about 5% of an anionic, polymeric suspending agent.

A further aspect of the present invention is to provide a new and improved method of making an aqueous conditioning shampoo having an anionic surfactant, a cationic nitrogen-containing conditioning agent, a suspended non-volatile silicone, and an anionic polymeric suspending agent by solubilizing the silicone or silicones in the quaternary nitrogen containing conditioning agent, and vigorously mixing the composition, together with the polymeric suspending agent, to suspend silicone droplets having a particle size in the range of about 5 microns to about 100 microns to provide new and unexpected stability to the conditioning shampoo composition, without sacrifice in foaming.

The above and other aspects and advantages of the present invention will become apparent from the following detailed description of the preferred embodiments.

DETAILED DESCRIPTION OF THE PREFERRED EMBODIMENTS

The aqueous conditioning shampoo composition of the present invention generally includes an anionic surfactant in an amount of about 5% to about 65% by weight of the composition; a cationic di-long chain alkyl quaternary ammonium salt in the amount of about 0.1% to about 20% by weight of the composition; a water-insoluble fatty alcohol in the amount of about 0.5% to about 10% by weight of the composition; one or more nonvolatile silicones in an amount of about 0.5% to about 10% by weight of the composition; and an anionic polymeric suspending agent, such as a cross-linked polyacrylic acid in the free acid form or partially or completely neutralized polyacrylic acid, in an amount of about 0.1% to about 5% by weight of the composition.

The conditioning shampoo of the present invention provides the hair with improved physical and cosmetic conditioning properties, such as gloss, thickness, softness, and manageability, including excellent wet and dry combing properties and body. As will be demonstrated more fully hereinafter, it is surprising and unexpected that the composition of the present invention, including an anionic cleansing compound, a cationic conditioning compound and a non-volatile silicone material remains stable, while achieving excellent cleansing and conditioning.

The anionic cleansing surfactant used in the composition and method of the present invention can be any of the anionic surfactants known or previously used in the art of hair shampoos. An anionic cleansing surfactant should be included in the composition of the present invention to effectively cleanse the hair and generates a high, stable foam level that consumers equate with cleaning efficiency. Nonionic and amphoteric surfactants are not as effective in cleansing the hair and do not provide the high foam level desired by consumers. However, optionally, nonionic, amphoteric and/or zwitterionic surfactants can be included in the compositions of the present invention in addition to one or more anionic surfactants, to help stabilize foam, to provide a suitable viscosity, or to give other functional or esthetic properties to the composition.

Usually, the anionic cleansing surfactant includes a hydrophobic moiety, such as a carbon chain including from about eight carbon atoms to about 30 carbon atoms, and particularly from about twelve carbon atoms to about twenty carbon atoms and further includes a hydrophilic moiety, such as a sulfate, sulfonate, carbonate, phosphate or carboxylate. Often, the hydrophobic carbon chain is etherified, such as with ethylene oxide or propylene oxide, to impart a particular physical property, such as increased water-solubility or reduced surface tension, to the anionic cleansing surfactant.

Suitable anionic cleansing surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates and isothienates; or combinations thereof. Many additional anionic cleansing surfactants are described in McCUTCHEON'S DETERGENTS and EMULSIFIERS, 1989 ANNUAL published by McCutcheon's Division MC Publishing Company, herein incorporated by reference. Usually, the anionic cleansing surfactant is present in the composition as a neutralized salt in the form of a sodium, potassium, lithium, ammonium, alkylammonium or hydroxyalkylammonium salt, wherein the alkyl moiety includes from one to about three carbon atoms. The alkyl sulfates and alkyl ether sulfates are particularly effective classes of anionic cleansing surfactants. Exemplary anionic cleansing surfactants that are useful in the composition and method of the present invention include, but are not limited to, the ammonium, monoethanolamine, diethanolamine, triethanolamine, isopropylamine, sodium, potassium, lithium, or magnesium salts of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or combinations thereof. An especially useful anionic cleansing surfactant is a mixture of a lauryl sulfate salt and a lauryl ester sulfate salt.

The emulsified conditioning shampoo of the present invention also includes a cationic water-insoluble, emulsifiable conditioning agent. The cationic conditioning agent used in the emulsified conditioning composition and method of the present invention is an oil-soluble, water-dispersible di-long chain alkyl quaternary ammonium salt, particularly a di-long chain alkyl, di-short chain alkyl quaternary ammonium salt. Oil soluble, water-dispersible quaternary ammonium compounds useful in the composition and method of the present invention are quaternary ammonium compounds having two long chain alkyl groups including from about 12 to about 22 carbon atoms. The long chains can be predominantly 12, 14, 16, 18, 20 and/or 22 carbon atoms in length and can be only one chain length or can be mixed chain lengths. The remaining two substitutions present on the quaternary nitrogen of the quaternary ammonium compound can be hydrogen; benzyl; short chain alkyl groups, having 1 to 4 carbon atoms such as methyl, ethyl, or hydroxyethyl; or combinations thereof, as long as the quaternary ammonium compound is oil-soluble and water-dispersible and contains two long chain alkyl substitutions, as defined.

The anion of the oil-soluble quaternary ammonium compound can be any anion, such as chloride, bromide, methyl sulfate, acetate, phosphate or nitrate, as long as the quaternary ammonium compound is oil-soluble.

In accordance with an important feature of the present invention, the oil-soluble, water-dispersible conditioning agent included in compositions of the present invention are those having a quaternary nitrogen atom and two long alkyl chains, having from about 12 to about 22 carbon atoms per alkyl chain. These conditioning agents include a wide range of compounds that can be broadly divided into groups based upon the structure of the substitution on the quaternary nitrogen atom, i.e., (a) compounds having two long carbon chains and one or two identical or different short chain alkyl groups having one to four, particularly one or two carbon atoms, and (b) compounds having two long carbon chains, one benzyl group and one short chain alkyl group having one to four, particularly one or two carbon atoms. The following list of oil-soluble quaternary ammonium compounds are exemplary, but not limiting, of oil-soluble di-long chain alkyl quaternary ammonium compounds that can be used in the composition and method of the present invention:

| | |
|---|---|
| Distearyldimethyl-ammonium chloride | (Distearyl dimonium chloride); |
| Distearyldimethyl-ammonium bromide | (Distearyl dimonium bromide) |
| Dicetyldimethyl-ammonium bromide | (Dicetyl dimonium bromide); |
| Dimethyldi-(hydrogenated tallow)-ammonium chloride | (Quaternium-18); |
| Dicetylmethylbenzyl-ammonium chloride; | |
| Dicetyldimethyl-ammonium chloride | (Dicetyl dimonium chloride) |
| Dicocodimethyl-ammonium chloride | (Dicoco dimonium chloride) |
| Dicocodimethyl-ammonium bromide | (Dicoco dimonium bromide) |
| Dibehenyl/diarachidyl-dimethyl ammonium chloride | (Dibehenyl/diarachidyl dimonium chloride) |
| Dibehenyl/diarachidyl-dimethyl ammonium bromide | (Dibehenyl/diarachidyl dimonium bromide) |
| Dibehenyl dimonium methyl sulfate | (Dibehenyl dimonium methyl sulfate) |
| Hydroxypropyl bis-stearyl-ammonium chloride | (Hydroxypropyl bis-stearyl dimonium chloride) |
| Dibehenyldimethyl-ammonium chloride; Dibehenylmethyl-benzyl-ammonium chloride; | (Dibehenyl dimonium chloride) |
| Dimyristyldimethyl-ammonium bromide; | (Dimyristyl dimonium bromide) |
| Dimyristyldimethyl-ammonium chloride | (Dimyristyl dimonium chloride) |

Wherein the name in parenthesis is the compound name given in the CTFA Dictionary 3rd ed., 1982.

It should be noted that the long alkyl chains of the oil-soluble quaternary ammonium compound are not commonly of a single chain length, but a mixture of chain lengths primarily within the $C_{12}$–$C_{22}$ range, e.g. $C_{12}$, $C_{14}$, $C_{16}$, $C_{18}$, $C_{20}$ and/or $C_{22}$. Generally, the oil-soluble quaternary ammonium compounds used in the compositions of the present invention have the long alkyl chains as a mixture of alkyl lengths. Such di-long chain alkyl quaternary ammonium compounds function in accordance with the principles of the present invention as long as the quaternary ammonium compound is oil-soluble and water-dispersible. Such conditioning agents are prepared conveniently from naturally occurring materials, such as tallow, coconut oil, soya oil and the like, or from synthetically produced mixtures which are known to include a mixture of long chain radicals.

The water-insoluble emulsifiable conditioning agent useful in the present invention should have the ability to separate from water and form a two-phase composition in water when the conditioning agent is mixed with water, prior to emulsification of the composition of the present invention. To achieve the full advantage of the present invention, the water-insoluble, emulsifiable quaternary ammonium conditioning agents used in the compositions of the present invention have a water-solubility of less than one percent. Such agents may be employed either as liquids or as solids.

Fatty alcohols useful in the present formulations are primary or secondary alcohols having about 8 to about 32 carbons, inclusive, either as single long chain lengths (e.g. 8, 10, 12, 14, 16, 18, 20, 22, 24, 26, 28 or 30 carbon atoms in length) or as a mixture of long chain lengths in any combination. The fatty alcohols can be straight chain, branched, saturated, and/or unsaturated structures and can be used alone or in admixture with each other. The preferred fatty alcohols are straight-chained, primary alcohols having about 10 to about 26 carbons, or mixtures of 10, 12, 14, 16, 18, 20, 22, 24 and/or 26 carbons including without limitation, lauryl, tridecyl, myristyl, cetyl, stearyl, oleyl, behenyl, arachyl, carnubyl, and ceryl alcohols, and combinations thereof. In addition, mixtures of natural or synthetic fatty alcohols having fatty chain lengths of from about 8 to about 32 carbons, inclusive, also are useful. Several such mixtures are commercially available, and are exemplified by a material containing a mixture of synthetic alcohols with 12 to 15 carbons in the alkyl chain sold under the trademark NEODOL 25 by Shell Chemical Company, and a material containing a mixture of synthetic alcohols with chain lengths of 12 to 16 carbons sold under the trademark ALFOL 1216 Alcohol by Conoco Chemicals.

Other suitable alcohols include the fatty alcohols of the above described carbon chain lengths which are ethoxylated to contain one to about three, and, preferably, and average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having *CTFA Dictionary* names of Ceteth-1 and Steareth-2, respectively.

The composition of the present invention also includes from about 0.15% to about 10%, and preferably from about 1.0% to about 5.0%, by weight of a non-volatile silicone compound. The preferred non-volatile silicone compound is a polydimethylsiloxane compound, such as a mixture, in about a 3:1 ratio, of a low molecular weight polydimethysiloxane fluid and a higher molecular weight polydimethylsiloxane gum. The non-volatile polydimethylsiloxane compound is added to the composition of the present invention in an amount sufficient to provide improved combing and improved feel (softness) to the hair after shampooing. As referred to herein, "silicone gums" are those non-functional siloxanes having a viscosity of from about 5 to about 600,000 centistokes at 25° C. The so-called rigid silicones, as described in U.S. Patent No. 4,902,499, herein incorporated by reference, having a viscosity above 600,000 centistokes at 20° C, e.g. 700,000 centistokes plus, and a weight average molecular weight of at least about 500,000 also are useful in accordance with the present invention.

Preferred silicone gums include linear and branched polydimethyl siloxanes, of the following general formula:

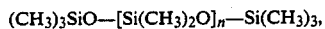

wherein n is from about 2,000 to about 15,000, preferably from about 2,000 to about 7,000. Silicone gums useful in compositions of the present invention are available from a variety of commercial sources, including General Electric Company and Dow Corning.

Examples of suitable preferred anionic, cross-linked polymeric suspending agents useful in the compositions and methods of the present invention include cross-linked polyacrylic acid and cross-linked metal salts of poylacrylic acid (partially or fully neutralized); and cross-linked maleic anhydride.

Any cross-linked, anionic polymer can be used as the suspending agent in the compositions and methods of the present invention. Suspending agents should suspend the silicone materials in the aqueous phase of the composition so that the composition remains stable at 120° F. for at least two weeks. Cross-linked anionic polymers useful for the compositions and methods of the present invention include those that have one or more substituents such as carboxylate, carboxy acid anhydride, sulfonate, sulfate, and/or phosphate, which in contact with water ionize to form polymeric ions with a substantial plurality of negatively charged sites. Examples of suitable cross-linked anionic polymers include:

styrene acrylate/ammonium methacrylate copolymers;
styrene/acrylate copolymers;
styrene/maleic anhydride copolymers;
ethylene/maleic anhydride copolymers;
polyacrylic acid;
styrene/acrylate/acrylonitrile copolymers;
styrene/acrylonitrile copolymers;
poly(vinyl sulfate);
poly(methacrylic acid);
poly(sodium 4-styrenesulfonate);
polyacrylonitrile; and the like.

Suitable organic polymers include, for example, polymeric water-soluble polyelectrolytes preferably having a molecular weight of at least 150,000 and containing a substantially linear carbon chain backbone derived by the polymerization of an aliphatic unsaturated group. These polymers are polymeric organic substances which, when contacted with an aqueous medium, will form organic ions having a substantial number of ionizable groups distributed at a plurality of positions thereon.

One type of compound useful in the practice of the invention is the equimolar copolymer of a polycarboxylic acid derivative and at least one other monomer copolymerizable therewith. The polycarboxylic acid derivative may be maleic anhydride, maleic acid, iumaric acid, itaconic acid, citraconic acid, aconitic acid, the amides of these acids, the alkali metal, alkaline earth metal and ammonium salts of these acids, the partial alkyl esters, salts of the partial alkyl esters and the substituted amides of these polycarboxylic acids. The carboxylic acid, carboxylic acid salt, amide and substituted amide radicals are the ionizable groups which contribute to the hydrophilic properties and tend to make the polymers anionic. The corresponding derivatives of methacrylic crotonic or other polymerizable acids also are useful, for example, a copolymer of dialkyl maleate and acrylic acid.

When the hydrophilic maleic acid, acrylic acid, and the like derivatives are used, hydrophobic comonomers may be used, for example, ethylene, propylene, isobutylene, styrene, α-methylstyrene, vinyl acetate, vinyl chloride, vinyl formate, vinyl alkyl ethers, alkyl acrylates and alkyl methacrylates. In the practice of this invention the dibasic polybasic acid derivatives of the copolymers may be, for example, maleic acid, maleic anhydride, sodium maleate, potassium maleate, ammonium maleate, calcium maleate, monosodium maleate, monopotassium maleate, monoammonium maleate, monocalcium maleate, and a monoalkyl maleate, maleic acid amide, the partial amide of maleic acid, the N-alkyl substituted maleic acid amide, the N-amino ethyl maleamide, the N-aminoethyl maleimide, the alkylaminoalkyl maleamides, and the corresponding derivatives of itaconic, catraconic, fumaric and aconitic acids. Any of the above-identified polybasic acid derivatives may be copolymerized with any of the other monomers described above, and any other monomer which forms a copolymer with di-basic acid derivatives. The polybasic acid derivatives may be copolymerized with a plurality of comonomers.

Other suitable cross-linked, anionic polymers are the polymers of acrylic or methacrylic acid derivatives, for example, acrylic acid, the alkali metal and ammonium salts of acrylic acid, methacrylic acid, the alkali metal and ammonium salts of methacrylic acid, acrylamide, methacrylamide, the N-alkyl substituted amides, the N-aminoalkylamides, and the corresponding N-alkylaminoalkyl substituted amides, the aminoalkyl acrylates, the aminoalkyl methacrylamides and the N-alkyl substituted aminoalkyl esters of either acrylic or methacrylic acids. These polymeric compositions may be the homopolymers or they may be copolymers with other copolymerizing monomers such as ethylene, propylene, isobutylene, styrene, α-methylstyrene, vinyl acetate, vinyl formate, alkyl ethers, acrylonitrile, methacrylonitrile, vinyl chloride, vinylidene chloride, the alkyl acrylates, the alkyl methacrylates, the alkyl maleates, and the alkyl fumarates, and other olefinic monomers copolymerizable therewith.

Another class of cross-linked anionic organic polymers are the polymers of vinyl sulfonic acid, and the copolymers of vinyl sulfonic acid with one or more polymerizable organic monomers, for example, vinyl chloride, acrylonitrile, styrene, vinyl acetate and other polymerizable mono-olefinic compounds. The sulfonic acid groups so introduced may be converted to sulfonic acid salts, acid amides or other electrolytic groupings. The copolymers of this type may involve the use of a plurality of sulfonic acid monomers and/or a plurality of the conventional comonomers as described.

The cross-linked anionic polymers should have a weight average molecular weight of at least about 50,000, preferably at least about 150,000, and best results are achieved when the cross-linked anionic suspending agent has a weight average molecular weight of at least about 1,000,000.

To achieve the best stability, a portion of the water and a portion of the anionic surfactant(s) are mixed first and heated to a temperature above the melting point of the fatty alcohol, e.g. 150°-200° F. The fatty alcohol then is added until it is completely dissolved in the water. The silicone or silicone blend then is added and the mixture is agitated vigorously to sheer and break up the silicone material into droplets preferably to a size less then about 10 micrometers, and more preferably to a size of about 5 microns to about 100 microns. The mixture is maintained at a temperature above the melting point of the fatty alcohol until all components are added. Prior to adding the di-long chain alkyl quaternary ammonium salt, it is preferred to increase the temperature up to about 175° F. to 190° F. After the silicone is dispersed and the temperature is increased to least about 175° F., preferably about 180° F. to about 185° F., the di-long chain alkyl quaternary ammonium salt is added, with agitation, to form an emulsion.

To achieve the best results, at the point that the silicone is sheared, the composition should have a viscosity in the range of about 5,000 to about 20,000 centipoises so that upon vigorous mixing or shearing, the resulting silicone droplets have a particle size of about 5 microns to about 100 microns, and preferably about 10 microns to about 30 microns, and are stable in the oil phase. As an example of the vigorous mixing, a six-bladed axial flow turbine impeller rotating at a speed of about 500 to 800 r.p.m. provides sufficient shearing of the non-volatile silicone material resulting in silicone droplets within the size range of about 5 to about 100 microns, and the sheared silicone droplets are exceptionally stable. Depending upon the quantity of anionic cross-linked polymeric suspending agent used, and the amount of water contained in the polymer, about 0 to about 20% of the water contained in the final composition can be withheld from the composition, together with a proportionate percentage of the anionic surfactant, if necessary to provide a sufficiently viscous composition to shear the silicone, e.g. 5,000 to 20,000 centipoises. To achieve the full advantage of the present invention at least a portion of the polymeric suspending agent should be contained in the composition when the silicone or silicone blend is sheared for best stability. The shearing of the silicone within a viscous composition provides the best silicone particle size and stability to the composition. If the particle size of the silicone droplets is less than about 5 microns, the silicone surface area is too great resulting in reduced foam. If the particle size of the silicone droplets is greater than about 100 microns, the silicone droplets have a tendency to coalesce and separate from the composition.

If some of the water and surfactant are withheld from the composition until after silicone shearing to maintain the composition sufficiently viscous during silicone dispersion, the remaining water and anionic surfactant(s) then are added, slowly, e.g. about 1 to about 3, preferably about 1 to 2, pounds per minute for a 250 pound shampoo batch, with gentle agitation.

Without being bound by any particular theory it is theorized that one or both of the long chain alkyl radicals from the di-long chain alkyl quaternary ammonium salt forms a complex with the anionic surfactant surrounding the silicone droplets, dispersed in the water phase, to aid in stabilizing the silicone suspension. The cross-linked anionic polymeric suspending agent appears to enter into this ionic complexing to aid in the suspending of the silicone droplets Whatever the mechanism, contrary to the prior art teachings, this complexing resulting in excellent suspension, works for the di-long chain alkyl quaternary ammonium salts but not for the mono-long chain alkyl or tri-long chain alkyl quaternary ammonium salts.

The following examples illustrate various conditioning shampoos made in accordance with the present invention:

| INGREDIENTS: | EXAMPLE 1 % WT. | EXAMPLE 1A % WT. |
| --- | --- | --- |
| cross-linked polyacrylic acid (CARBOPOL ® 1342) (1.5% active) | 25.0 | 25.0 |
| sodium laureth sulfate (30% active) | 25.0 | 25.0 |
| cocamide MEA | 2.0 | 2.0 |
| cetyl/stearyl alcohol | 2.0 | 2.0 |
| non-volatile silicone blend 25% SE-30 GUM 75% SF-96-50 oil | 3.0 | 3.0 |
| distearyl dimethyl ammonium chloride (AROSURF ® TA-100) | 1.5 | 1.5 |

-continued

| | | |
|---|---|---|
| ammonium lauryl sulfate (30% active) | 27.50 | 27.50 |
| sodium laureth sulfate (30% active) | 2.50 | 2.50 |
| ammonium xylene sulfonate | 2.00 | 2.00 |
| soft water | 6.4236 | 6.4236 |
| isopropyl myristate | 2.00 | — |
| lauryl alcohol | — | 2.00 |
| NaOH (50% active) | 0.25 | 0.25 |
| F D & C green #3 (1% active) | 0.0064 | 0.0064 |
| D & C yellow #10 (1% active) | 0.170 | 0.170 |
| fragrance (1% active) | 0.50 | 0.50 |
| KATHON ® CG | 0.05 | 0.05 |
| GLYDANT ® | 0.10 | 0.10 |

PROCEDURE:
(1.) Add CARBOPOL slurry, and SLS to tank, begin heating to 180–185° F. with moderate agitation.
(2.) At 140–150° F., add cocamide MEA, mix until melted.
(3.) At 160–165° F. add cetyl/stearyl alcohol, mix until melted.
(4.) Add Silicone Blend when fatty alcohol has melted. Increase agitation to shear silicone blend into droplets, at 180–185° F. Mix.
(5.) At 180–185° F., add AROSURF ®, mix for ½ hour to one hour or until a smooth glossy appearance is seen and composition has a viscosity of at least 5,000 cps.
(6.) Very slowly add the remaining anionic surfactants, turn off heat and slow down agitation.
(7.) Add isopropyl myristate, mix 10 min–15 min, add NaOH 50%.
(8.) Add dye, then remaining ingredients at 110° F.

SPECS: pH 80° F.: 5.5–6.0, TA 80° F.: 30,000 cps–60,000 cps
Viscosity, 80° F.: 5,000–8,000 cps.

EXAMPLE 2-5 (wt. %)

| INGREDIENTS: | 2 | 3 | 4 | 5 |
|---|---|---|---|---|
| cross-linked polyacrylic acid (CARBOPOL ® 1342) (1.5% active) | 25.0 | 25.0 | 25.0 | 25.0 |
| ammonium lauryl sulfate (30% active) | 20.0 | — | 20.0 | — |
| sodium laureth sulfate (30% active) | — | 20.0 | — | 20.0 |
| ammonium xylene sulfonate | 4.0 | — | 4.0 | — |
| cocamide DEA | 2.0 | 2.0 | 2.0 | 2.0 |
| cetyl/stearyl alcohol | 2.0 | 2.0 | 2.5 | 2.5 |
| non-volatile silicone blend 25% SE-30 GUM 75% SF-96-50 oil | 3.0 | 3.0 | 3.0 | 3.0 |
| dicetyl dimethyl ammonium chloride (ADOGEN ® 432 PG) (67% active) | 2.24 | 2.24 | 2.24 | 2.24 |
| ammonium lauryl sulfate (30% active) | 35.0 | 27.5 | 35.0 | 32 |
| sodium laureth sulfate | — | 7.5 | — | 7.5 |

-continued

| | | | | |
|---|---|---|---|---|
| (30% active) | | | | |
| soft water | 3.8336 | 7.8336 | 3.3336 | 7 |
| isopropyl myristate | 2.0 | 2.0 | 2.0 | 2 |
| NaOH (50% active) | 0.25 | 0.25 | 0.25 | 0 |
| F D & C green #3 (1% active) | 0.0064 | 0.0064 | 0.0064 | 0 |
| D & C yellow #10 (1% active) | 0.170 | 0.17 | 0.17 | 0 |
| Fragrance (1% active) | 0.35 | 0.35 | 0.35 | 0 |
| GLYDANT ® | 0.10 | 0.10 | 0.10 | 0 |
| KATHON ® CG | 0.05 | 0.05 | 0.05 | 0 |
| Initial Adjustments | — | +1% AXS* | +2% AXS* | |
| pH 80° F. | 5.9 | 6.0 | 6.0 | |
| Viscosity 80° F. | 10,000 cps | 8,000 cps | 7,800 cps | |
| TA | — | 60,000 cps | 60,000 cps | |
| Adjustments | +1% AXS | — | — | |
| Viscosity 80° F. | 8,000 cps | | | |
| Final Viscosity | 8,000 cps | 8,000 cps | 7,800 cps | |
| TA | 60,000 cps | 60,000 cps | 60,000 cps | |
| SPECS: | pH 80° F. | 5.5–6.0 | | |
| | Viscosity | 5,000–8,000 cps | | |
| | TA | 30,000–60,000 cps | | |

*ammonium xylene sulfonate

EXAMPLE 6-7 (wt. %)

| INGREDIENTS: | 6 | 7 |
|---|---|---|
| cross-linked polyacrylic acid (CARBOPOL ® 1342) (1.5% active) | 25.0 | 25.0 |
| ammonium lauryl ether sulfate/lauramide DEA blend (38.2% active) | 13.0 | — |
| sodium laureth sulfate (30% active) | 20.0 | 31.0 |
| lauramide DEA | — | 2.0 |
| cetyl/stearyl alcohol | 3.5 | 3.5 |
| non-volatile silicone blend 25% SE-30 GUM 75% SF-96-50 oil | 3.0 | 3.0 |
| distearyl dimethyl ammonium chloride (AROSURF ® TA-100) | 1.0 | 1.0 |
| sodium laureth sulfate (30% active) | 11.0 | — |
| lauramide DEA | 2.0 | — |
| ammonium lauryl sulfate (30% active) | — | 31.0 |
| ammonium xylene sulfonate | 5.0 | — |
| soft water | 0.4236 | 0.4236 |
| isopropyl myristate | 2.0 | 2.0 |
| NaOH (50% active) | 0.25 | 0.25 |
| F D & C green #3 (1% active) | 0.0064 | 0.0064 |
| D & C yellow #10 (1% active) | 0.170 | 0.170 |
| Fragrance (1% active) | 0.50 | 0.50 |
| KATHON ® CG | 0.05 | 0.05 |
| GLYDANT ® | 0.10 | 0.10 |
| Initial Adjustment | +1% AXS | not made |
| RESULTS: | pH 80° F.: | 5.9 |
| | TA 80° F.: | 100,000 cps |
| | Viscosity: | 8,800 cps |
| SPECS: | pH 80° F.: | 5.5–6.0 |
| | TA 80° F.: | 50,000–100,000 cps |
| | Viscosity: | 5,000–9,000 cps |

EXAMPLES 8-16 (% WT.)

| EXAMPLE | 8 | 9 | 10 | 11 | 12 | 13 | 14 | 15 | 16 |
|---|---|---|---|---|---|---|---|---|---|
| Cross-linked polyacrylic acid (CARBOPOL ® 1342) (1.5% active) | 25 | 25 | 25 | 25 | 25 | 25 | 25 | 25 | 25 |
| ammonium | 20 | 20 | 20 | 20 | 20 | 20 | 20 | 20 | 20 |

-continued

| | | | | | | | | | |
|---|---|---|---|---|---|---|---|---|---|
| lauryl sulfate (30% active) | | | | | | | | | |
| cocamide DEA | 2.0 | — | — | 2.0 | — | — | 2.0 | — | — |
| cocamide MEA | — | 2.0 | — | — | 2.0 | — | — | 2.0 | — |
| lauramide DEA | — | — | 2.0 | — | — | 2.0 | — | — | 2.0 |
| cetyl/stearyl alcohol | 2.0 | 2.0 | 2.0 | 2.0 | 2.0 | 2.0 | 2.0 | 2.0 | 2.0 |
| non-volatile silicone blend 25% SE-30 GUM 75% SF-96-50 oil | 3.0 | 3.0 | 3.0 | 3.0 | 3.0 | 3.0 | 3.0 | 3.0 | 3.0 |
| distearyl dimethyl ammonium chloride (AROSURF ® TA-100) | 1.0 | 1.0 | 1.0 | 1.0 | 1.0 | 1.0 | 1.0 | 1.0 | 1.0 |
| ammonium lauryl sulfate (30% active) | 35 | 35 | 35 | 35 | 35 | 35 | 35 | 35 | 35 |
| isopropyl myristate | 2.0 | 2.0 | 2.0 | 2.0 | 2.0 | 2.0 | 2.0 | 2.0 | 2.0 |
| soft water | 9.15 | 9.15 | 9.15 | 9.15 | 9.15 | 9.15 | 9.15 | 9.15 | 9.15 |
| NaOH (50% active) | 0.25 | 0.25 | 0.25 | 0.25 | 0.25 | 0.25 | 0.25 | 0.25 | 0.25 |
| F D & C orange #4 (1% active) | 0.10 | 0.10 | 0.10 | 0.10 | 0.10 | 0.10 | 0.10 | 0.10 | 0.10 |
| fragrance (1% active) | 0.35 | 0.35 | 0.35 | 0.35 | 0.35 | 0.35 | 0.35 | 0.35 | 0.35 |
| GLYDANT ® | 0.10 | 0.10 | 0.10 | 0.10 | 0.10 | 0.10 | 0.10 | 0.10 | 0.10 |
| KATHON ® CG | 0.05 | 0.05 | 0.05 | 0.05 | 0.05 | 0.05 | 0.05 | 0.05 | 0.05 |
| Initial Adjustments | | | | | | | +5% AXS* | +5% AXS* | +5% AXS* |
| pH 80° F. | | | | | | | 6.0 | 5.7 | 6.0 |
| Viscosity 80° F. | | | | | | | 8,100 cps | 11,000 cps | 7,600 cps |
| Let compositions sit overnight | | | | | | | | | |
| Viscosity 80° F. | | | | | | | 13,000 | 13,400 | 12,200 |
| Adjustments | | | | | | | +2% AXS* | +2% AXS* | +2% AXS* |
| pH 80° F. | | | | | | | 6.0 | 5.7 | 6.0 |
| Viscosity 80° F. | | | | | | | 6,000 cps | 6,500 cps | 4,800 cps |
| TA | | | | | | | 64,000 cps | 72,000 cps | 52,000 cps |
| SPECS: | pH 80° F.: 5.5–6.0 | | | | | | | | |
| | Viscosity 80° F.: 5,000–8,000 cps | | | | | | | | |

*ammonium xylene sulfonate

| EXAMPLES 17-20 (Actual wt. %) | | | | |
|---|---|---|---|---|
| | EXAMPLE: | | | |
| INGREDIENTS: | 17 | 18 | 19 | 20 |
| cross-linked polyacrylic acid (CARBOPOL ® 1342) (1.5% active) | 32.0 | 32.0 | 32.0 | 32.0 |
| ammonium lauryl ether sulfate/ lauramide DEA blend (38.2% active) | 13.0 | 13.0 | 13.0 | 13.0 |
| ammonium lauryl sulfate *30% active) | 7.0 | 7.0 | 7.0 | 7.0 |
| cetyl/stearyl alcohol | 2.0 | 2.5 | 3.0 | 3.5 |
| non-volatile silicone blend 25% SE-30 GUM 75% SF-96-50 oil | 3.0 | 3.0 | 3.0 | 3.0 |
| distearyl dimethyl ammonium chloride (AROSURF ® TA-100) | 1.0 | 1.0 | 1.0 | 1.0 |
| ammonium lauryl sulfate (30% active) | 31.0 | 31.0 | 31.0 | 31.0 |
| isopropyl myristate | 2.0 | 2.0 | 2.0 | 2.0 |
| ammonium xylene sulfonate | 1.0 | 1.0 | 1.0 | 1.0 |
| soft water | 7.3 | 6.8 | 6.3 | 5.8 |
| NaOH (50% active) | 0.2 | 0.2 | 0.2 | 0.2 |
| fragrance (1% active) | 0.35 | 0.35 | 0.35 | 0.35 |
| GLYDANT ® | 0.10 | 0.10 | 0.10 | 0.10 |
| KATHON ® CG | 0.05 | 0.05 | 0.05 | 0.05 |

OBSERVATIONS

Examples 18–20 had very thick oil phases with the addition of cetyl/stearyl alcohol. Three percent ammonium lauryl sulfate was added to Example 18 oil phase and 8% was added to Examples 19 and 20. With addition of AROSURF ®, all Examples were too thick. 5% ammonium lauryl sulfate was then added to all Examples which gave a good mixable oil phase. Adjustments in viscosities were made by the addition of 2% ammonium xylene sulfonate to Example #13, 3% ammonium xylene sulfonate to Example #18, 5% ammonium xylene sulfonate to Example #19, and 7.5% ammonium xylene sulfonate to Example #20.

| RESULTS: | 17 | 18 | 19 | 20 |
|---|---|---|---|---|
| pH 80° F. | 5.5 | 5.5 | 5.5 | 5.5 |
| Viscosity 80° F. | 7,600 cps | 7,000 cps | 6,800 cps | 7,000 cps |
| TA 80° F. | 56,000 cps | 60,000 cps | 60,000 cps | 64,000 cps |
| SPECS: | pH: 5.5–6.0 | | | |
| | Viscosity 80° F.: 5,000–8,000 cps | | | |

TA: 30,000–70,000 cps

The suspending results achieved in accordance with the present invention are particularly surprising in view of the Declaration filed (paper No. 7) in the file history of the Oh et al. U.S. Pat. No. 4,704,272. This Declaration made it clear that the di-long chain alkyl quaternary ammonium salts could not be effectively incorporated in conditioning shampoos containing one or more non-volatile silicones because of very poor stability. The following compositions in TABLE I (PRIOR ART) compared in the Oh et al, file history, and the stability results that follow, teach those skilled in the art to avoid the use of di-long chain quaternary ammonium salts in a conditioning shampoo containing non-volatile silicones:

TABLE I
(PRIOR ART)

| COMPONENT | ACTUAL WT. % | |
|---|---|---|
| Ammonium lauryl sulfate | 12.00 | 12.00 |
| Ammonium laureth (3) sulfate | 4.00 | 4.00 |
| Ammonium xylene sulfonate | 2.20 | 2.20 |
| Cetearyl alcohol | 1.00 | 1.00 |
| Glycol distearate | 0.75 | 0.75 |
| Cocamide MEA | 1.00 | 1.00 |
| Xanthan gum | 0.75 | 0.75 |
| Dimethicone mixture | 3.00 | 3.00 |
| Tricetylmethyl ammonium chloride | 0.50 | — |
| Ditallow dimethyl ammonium chloride | — | 0.50 |
| Color, perfume, minors, water | q.s. to 100% | |

"That when these compositions were placed in clear glass bottles and stored for two weeks at 35° F., 50° F. or 80° F., the following results were obtained:"

| Temperature | Present (Oh et al.) Invention | Prior Art |
|---|---|---|
| 35° F. | No visible separation Composition had normal appearance | Clear layer at top of composition. The composition had curdled appearance |
| 50° F. | No visible separation Composition had normal appearance | Clear layer at top of composition. The composition had curdled appearance |
| 80° F. | No visible separation Composition had normal appearance | Clear layer at top of composition. The composition had curdled appearance |

Quite to the contrary, applicants have found that in a conditioning shampoo composition containing an anionic polymeric suspending agent, or guar gum, and one or more non-volatile silicones, a di-long chain alkyl quaternary ammonium salt is needed, since a tri-long chain alkyl quaternary ammonium salt does not provide sufficient stability, as shown in comparative Examples 21 and 22:

EXAMPLE 21-22 (wt. %)

| | EXAMPLE | |
|---|---|---|
| | 21 | 22 |
| INGREDIENTS: | | |
| Cross-linked polyacrylic acid (CARBOPOL ® 1342) (1.5% active) | 25.0 | 25.0 |
| ammonium lauryl sulfate (30% active) | 20.0 | 20.0 |
| cocamide DEA | 2.0 | 2.0 |
| cetyl/stearyl Alcohol | 2.0 | 2.0 |
| non-volatile silicone blend 25% SE-30 GUM 75% SF-96-50 oil | 3.0 | 3.0 |
| dicetyl dimethyl ammonium chloride (ADOGEN ® 432 PG) (67% active) | 2.27 | — |
| tricetyl methyl ammonium chloride | — | 1.5 |
| ammonium lauryl sulfate (30% active) | 35.0 | 35.0 |
| isopropyl myristate | 2.0 | 2.0 |
| soft water | 8.16 | 8.9 |
| NaOH 50% | 0.25 | 0.25 |
| FD & C orange #4 (1%) | 0.10 | 0.10 |
| Fragrance | 0.35 | 0.35 |
| KATHON ® CG | 0.05 | 0.05 |
| GLYDANT ® | 0.10 | 0.10 |
| ADJUSTMENTS | +4% AXS* | +4% AXS* |
| RESULTS: | | |
| pH 80° F. | 5.8 | 5.8 |
| viscosity | 8,400 cps | 12,800 cps, +2% AXS |
| TA | 64,000 cps | 108,000 cps |
| Final Viscosity After four days at 120° F. | 8,400 cps | 7,300 cps |
| Example 22 has separated Example 21 looks good. After 2 weeks at 120° F. | | |
| Example 21 is stable | | |
| SPECS: | | |
| pH 80° F.: 5.5–6.0 | viscosity - 5,000–8,000 cps | |

*ammonium xylene sulfonate

The following Examples 23–32 conclusively show that the mono-long chain and tri-long chain alkyl quaternary ammonium salts do not form compositions that are sufficiently stable:

| | WT. % |
|---|---|
| EXAMPLE 23 | |
| COMPONENT | |
| cross-linked polyacrylic acid (CARBOPOL ® 1342 1.5% slurry) | 25.00 |
| ammonium lauryl sulfate (30% active) | 25.00 |
| cocamide MEA | 1.00 |
| non-volatile silicone blend 25% SE-30 GUM 75% SF-96-50 oil | 3.00 |
| cetyl & stearyl alcohol | 2.00 |
| polymethacrylamidopropyl trimonium chloride (LEXQUAT ® 2240) | 6.00 |
| isopropyl myristate | 2.00 |
| ammonium lauryl sulfate (30% active) | 30.00 |
| sodium hydroxide, (50%) | 0.25 |
| soft water | 5.15 |
| D&C orange #4 (100%) | 0.10 |
| fragrance | 0.35 |
| methyl & chloromethyl isothiazolinone | 0.05 |
| GLYDANT ® | 0.10 |
| RESULTS: | |
| Separated @ 120° F. in 1 day @ 110° F. in 2 days | |
| EXAMPLE 24 | |
| COMPONENT | |
| cross-linked polyacrylic acid (CARBOPOL ® 1342 1.5% slurry) | 25.00 |

-continued

| | WT. % |
|---|---|
| ammonium lauryl sulfate (30% active) | 25.00 |
| cocamide MEA | 1.00 |
| non-volatile silicone blend | 3.00 |
| 25% SE-30 GUM | |
| 75% SF-96-50 oil | |
| cetyl & stearyl alcohol | 2.00 |
| polyquaternium 22 (MERQUAT ® 280) | 4.30 |
| isopropy myristate | 2.00 |
| ammonium lauryl sulfate (30% active) | 30.00 |
| sodium hydroxide, (50%) | 0.25 |
| soft water | 6.85 |
| D&C orange #4 (100%) | 0.10 |
| fragrance | 0.35 |
| methyl & chloromethyl isothiazolinone | 0.05 |
| GLYDANT ® | 0.10 |

RESULTS:
Separated @ 120° F. in 1 day
@ 110° F. in 2 days

EXAMPLE 25

COMPONENT

| | WT. % |
|---|---|
| cross-linked polyacrylic acid (CARBOPOL ® 1342 1.5% slurry) | 25.00 |
| ammonium lauryl sulfate (30% active) | 25.00 |
| cocamide MEA | 1.00 |
| non-volatile silicone blend | 3.00 |
| 25% SE-30 GUM | |
| 75% SF-96-50 oil | |
| cetyl & stearyl alcohol | 2.00 |
| methylbis (2-hydroxy ethyl) cocoammonium chloride (VARIQUAT ® 638) | 2.00 |
| isopropyl myristate | 2.00 |
| ammonium lauryl sulfate (30% active) | 30.00 |
| sodium hydroxide, 50% | 0.25 |
| soft water | 9.15 |
| D&C orange #4 (100%) | 0.10 |
| fragrance | 0.35 |
| methyl & chloromethyl isothiazolinone | 0.05 |
| GLYDANT ® | 0.10 |

RESULTS:
Separated @ 120° F. in 12 days.

EXAMPLE 26

COMPONENT

| | WT. % |
|---|---|
| cross-linked polyacrylic acid (CARBOPOL ® 1342 1.5% slurry) | 25.00 |
| ammonium lauryl sulfate (30% active) | 25.00 |
| cocamide MEA | 1.00 |
| non-volatile silicone blend | 3.00 |
| 25% SE-30 GUM | |
| 75% SF-96-50 oil | |
| cetyl & stearyl alcohol | 2.00 |
| QUATERNIUM-_ (75%)/FINQUAT ® -(25%) | 6.00 |
| isopropyl myristate | 2.00 |
| ammonium lauryl sulfate (30% active) | 30.00 |
| sodium hydroxide, (50%) | 0.25 |
| soft water | 5.15 |
| D&C orange #4 (100%) | 0.10 |
| fragrance | 0.35 |
| methyl & chloromethyl isothiazolinone | 0.05 |
| GLYDANT ® | 0.10 |

RESULTS:
Separated @ 120° F. in 5 days

EXAMPLE 27

COMPONENT

| | WT. % |
|---|---|
| cross-linked polyacrylic acid (CARBOPOL ® 1342 1.5% slurry) | 25.00 |
| ammonium lauryl sulfate (30% active) | 25.00 |
| cocamide MEA | 1.00 |
| non-volatile silicone blend | 3.00 |
| 25% SE-30 GUM | |
| 75% /SF-96-50 oil | |
| cetyl & stearyl alcohol | 2.00 |
| QUATERNIUM-18 HECTORITE | 1.50 |
| isopropyl myristate | 2.00 |
| ammonium lauryl sulfate (30% active) | 30.00 |
| sodium hydroxide, (50%) | 0.25 |
| soft water | 9.65 |
| D&C orange #4 (100%) | 0.10 |
| fragrance | 0.35 |

-continued

| | WT. % |
|---|---|
| methyl & chloromethyl isothiazolinone | 0.05 |
| GLYDANT ® | 0.10 |

RESULTS:
Separated @ 120° F. in 4 days

EXAMPLE 28

COMPONENT

| | WT. % |
|---|---|
| cross-linked polyacrylic acid (CARBOPOL ® 1342 1.5% slurry) | 25.00 |
| ammonium lauryl sulfate (30% active) | 25.00 |
| cocamide MEA | 1.00 |
| cetyl & stearyl alcohol | 2.00 |
| non-volatile silicone blend | 3.00 |
| 25% SE-30 GUM | |
| 75% SF-96-50 oil | |
| quaternized heptadecyl imidazoline | 1.50 |
| isopropyl myristate | 2.00 |
| ammonium lauryl sulfate (30% active) | 30.00 |
| sodium hydroxide, (50%) | 0.25 |
| soft water | 9.65 |
| D&C orange #4 (100%) | 0.10 |
| fragrance | 0.35 |
| methyl & chloromethyl isothiazolinone | 0.05 |
| GLYDANT ® | 0.10 |

RESULTS:
Began to separate after 3 days at 120° F.
Separated after 4 days at 120° F.

EXAMPLE 29

COMPONENT

| | WT. % |
|---|---|
| cross-linked polyacrylic acid (CARBOPOL ® 1342 1.5% slurry) | 25.00 |
| ammonium lauryl sulfate (30% active) | 25.00 |
| cocamide MEA | 1.00 |
| cetyl & stearyl alcohol | 2.00 |
| non-volatile silicone blend | 3.00 |
| 25% SE-30 GUM | |
| 75% SF-96-50 oil | |
| tricetyl ammonium chloride (VARISOFT TC 9) | 1.50 |
| isopropyl myristate | 2.00 |
| ammonium lauryl sulfate | 30.00 |
| sodium hydroxide, (50%) | 0.25 |
| soft water | 9.65 |
| D&C orange #4 (100%) | 0.10 |
| fragrance | 0.35 |
| methyl & chloromethyl isothiazolinone | 0.05 |
| GLYDANT ® | 0.10 |

MANUFACTURING STEPS:
(1) Add CARBOPOL ® and ammonium lauryl sulfate, start heating to 180° F.
(2) At about 130° F. add cocamide MEA.
(3) At about 170° F. add cetyl/stearyl alcohol, mix until dissolved.
(4) Add silicone blend.
(5) At 180° F. add quat, mix for ½ hour.
(6) After ½ hour and when batch is smooth and shiny turn off heat, add ammonium laurylsulfate slowly.
(7) Add isopropyl myristate.
(8) Add water, NaOH, color.
(9) At about 110° F. add fragrance, and preservatives.

RESULTS:
Separated after 3 days at 120° F.,
Separated after 4 days at 110° F.

EXAMPLE 30

COMPONENT

| | WT. % |
|---|---|
| cross-linked polyacrylic acid (CARBOPOL ® 1342 1.5% slurry) | 25.00 |
| ammonium lauryl sulfate (30% active) | 25.00 |
| cocamide MEA | 1.00 |
| cetyl & stearyl alcohol | 2.00 |
| non-volatile silicone blend | 3.00 |
| 25% SE-30 GUM | |
| 75% SF-96-50 oil | |
| oleamidopropyl dihydroxypropyl dimonium chloride | 6.00 |
| isopropyl myristate | 2.00 |
| ammonium lauryl sulfate (30% active) | 30.00 |

-continued

| | WT. % |
|---|---|
| sodium hydroxide, (50%) | 0.25 |
| soft water | 10.15 |
| D&C orange #4 (100%) | 0.10 |
| fragrance | 0.35 |
| methyl & chloromethyl isothiazolinone | 0.05 |
| GLYDANT ® | 0.10 |
| RESULTS: | |
| Separated after 3 days at 120° F., | |
| Separated after 4 days at 110° F. | |

EXAMPLE 31

| COMPONENT | |
|---|---|
| cross-linked polyacrylic acid (CARBOPOL ® 1342 1.5% slurry) | 25.00 |
| ammonium lauryl sulfate (30% active) | 25.00 |
| cocamide MEA | 1.00 |
| non-volatile silicone blend 25% SE-30 GUM 75% SF-96-50 oil | 3.00 |
| cetyl & stearyl alcohol | 2.00 |
| bishydroxyethyl dihydroxypropyl stearamide | 5.00 |
| isopropyl myristate | 2.00 |
| ammonium lauryl sulfate (30% active) | 30.00 |
| sodium hydroxide, (50%) | 0.25 |
| soft water | 6.15 |
| D&C orange #4 (100%) | 0.10 |
| fragrance | 0.35 |
| methyl & chloromethyl isothiazolinone | 0.05 |
| GLYDANT ® | 0.10 |
| RESULTS: | |
| Separated @ 120° F. in 6 days. | |

EXAMPLE 32

| COMPONENT | |
|---|---|
| cross-linked polyacrylic acid (CARBOPOL ® 1342 1.5% slurry) | 25.00 |
| ammonium lauryl sulfate (30% active) | 25.00 |
| cocamide MEA | 1.00 |
| non-volatile silicone blend 25% SE-30 GUM 75% SF-96-50 oil | 3.00 |
| cetyl/stearyl alcohol | 2.00 |
| cetrimonium chloride | 5.00 |
| isopropyl myristate | 2.00 |
| ammonium lauryl sulfate (30% active) | 30.00 |
| sodium hydroxide, (50%) | 0.25 |
| soft water | 6.15 |
| D&C orange #4 (100%) | 0.10 |
| fragrance | 0.35 |
| methyl & chloromethyl isothiazolinone | 0.05 |
| GLYDANT ® | 0.10 |
| RESULTS: Separated in 10 days @ 120° F. | |

Various other polymeric suspending agents, glycol and glycerol stearates and amine oxides were substituted for the CARBOPOL ® 1342 to determine their effectiveness, as shown in the following example 33–43, but only the anionic cross-linked polymers and guar gum were effective in providing stability for at least 2 weeks at 120° F.

EXAMPLE 33
FORMULATION:

| ITEM | COMPONENT | % WT. |
|---|---|---|
| A{1 | CARBOPOL ® 1342 Slurry (2.0% active) | 20.00 |
| A{2 | ammonium lauryl sulfate (30% active) | 10.00 |
| A{3 | cocamide MEA | 2.00 |
| A{4 | isopropyl myristate | 2.00 |
| B{5 | ammonium lauryl sulfate (30% active) | 14.00 |
| B{6 | distearyl dimethyl ammonium chloride (AROSURF ® TA-100) | 1.50 |
| B{7 | non-volatile silicone blend 25% SE-30 GUM 75% SR-96-50 oil | 3.00 |
| B{8 | cetyl & stearyl alcohol | 2.00 |
| B{9 | ammonium xylene sulfonate | 2.00 |
| C{10 | ammonium lauryl sulfate (30% active) | 31.00 |
| C{11 | soft water | 11.65 |
| C{12 | D & C orange #4 (1%) | 0.10 |
| C{13 | Fragrance | 0.35 |
| C{14 | KATHON ® | 0.05 |
| C{15 | GLYDANT ® | 0.10 |
| C{16 | NaOH (50%) | 0.25 |

MIXING PROCEDURE (EXAMPLE 33)

In an 800 ml beaker, combine items #1 through #4, as composition A, while stirring and heating to 155° F. In a separate 600 ml beaker, composition B, heat #5 to 180° F. and then add #6. After all AROSURF® is dissolved, add #7, #8 and #9 and cool to 155° F. In a separate 1500 ml beaker, composition C, combine #10 through #15 while stirring at room temperature. Add composition (A) at 155° F. to composition (C) at room temperature and mix well. Add composition (B) at 155° F. to combined compositions (A) and (C). Add #16 and cool to 90° F.

| RESULTS (EXAMPLE 33): | |
|---|---|
| pH 80° F. | 5.5 |
| Viscosity | 10,000 cps |
| TA | 66,000 cps |
| Viscosity* | 6,900 cps |
| TA* | 46,000 cps |

*after +1.5% ammonium xylene sulfonate

After two weeks, the viscosity had reduced to about 3500 cps. since the Carbopol was not contained in the composition containing the silicone when the silicone was sheared. The composition can be made stable by shearing the components in a colloid mill, regardless of the order of addition.

EXAMPLES 34–36
FORMULATION:

| ITEM | COMPONENT | 34 WT. % | 35 WT. % | 36 WT. % |
|---|---|---|---|---|
| 1 | METHOCEL ® slurry (hydroxypropylmethyl-cellulose) (2.0% active) | 20.00 | — | — |
| 1A | NATROSOL ® slurry (Hydroxyethycellulose) (2.0% active) | — | 20.00 | — |
| 1B | GALACTOSOL ® slurry (Guar Gum) (2.0% active) | — | — | 20.00 |
| 2 | ammonium lauryl sulfate (30% active) | 25.00 | 25.00 | 25.00 |
| 3 | cocamide MEA | 2.00 | 2.00 | 2.00 |
| 4 | cetyl & stearyl alcohol | 2.00 | 2.00 | 2.00 |
| 5 | non-volatile silicone blend 25% SE-30 GUM 75% SF-96-50 oil | 3.00 | 3.00 | 3.00 |
| 6 | AROSURF ® TA-100 | 1.50 | 1.50 | 1.50 |
| 7 | ammonium lauryl sulfate (30% active) | 30.00 | 30.00 | 30.00 |
| 8 | ammonium xylene sulfonate | 2.00 | 2.00 | 2.00 |
| 9 | soft water | 11.65 | 11.65 | 11.65 |

-continued

| 10 | isopropyl myristate | 2.00 | 2.00 | 2.00 |
|---|---|---|---|---|
| 11 | NaOH (50%) | 0.25 | 0.25 | 0.25 |
| 12 | D & C orange #4 (1%) | 0.10 | 0.10 | 0.10 |
| 13 | fragrance | 0.35 | 0.35 | 0.35 |
| 14 | KATHON ® CG | 0.05 | 0.05 | 0.05 |
| 15 | GLYDANT ® | 0.10 | 0.10 | 0.10 |
|  |  | 100.00 | 100.00 | 100.00 |

RESULTS (Examples 34-36):
Example 34 was discarded due to overnight separation at room temperature
Example 35:

| pH at 80° F. | 8.34 |
|---|---|
| pH + 20 drops of citric acid | 7.86 |
| pH after 30 drops of citric acid | 5.79 |
| viscosity at pH 5.79 | 1,650 cps |
| TA | 8,000 cps | separated before two weeks at 120° F.
Example 36:

| pH at 80° F. | 8.24 |
|---|---|
| pH + 20 drops citric acid | 7.86 |
| viscosity at pH 5.73 | 3,400 cps |
| TA | 28,000 cps |

No separation at 120° F. after 2 weeks.

EXAMPLES 37 AND 38

| ITEM | COMPONENT | 37 WT. % | 38 WT. % |
|---|---|---|---|
| 1 | CARBOPOL ® 940 slurry | 20.00 | — |
| 1A | CARBOPOL ® 934 slurry | — | 20.00 |
| 2 | ammonium lauryl sulfate (30% active) | 25.00 | 25.00 |
| 3 | cocamide MEA | 2.00 | 2.00 |
| 4 | cetyl & stearyl alcohol | 2.00 | 2.00 |
| 5 | non-volatile silicone blend | 3.00 | 3.00 |
|  | 25% SE-30 GUM 74% SF-96-50 oil |  |  |
| 6 | AROSURF ® TA-100 | 1.50 | 1.50 |
| 7 | ammonium lauryl sulfate (30% active) | 30.00 | 30.00 |
| 8 | ammonium xylene sulfonate | 2.00 | 2.00 |
| 9 | soft water | 11.65 | 11.65 |
| 10 | isopropyl myristate | 2.00 | 2.00 |
| 11 | NaOH (50%) | 0.25 | 0.25 |
| 12 | D & C orange #4 (1%) | 0.10 | 0.10 |
| 13 | fragrance | 0.35 | 0.35 |
| 14 | KATHON ® CG | 0.05 | 0.05 |
| 15 | GLYDANT ® | 0.10 | 0.10 |
|  |  | 100.00 | 100.00 |

RESULTS (Examples 37 and 38):
Example 37

| pH at 80° F. | 5.80 |
|---|---|
| viscosity | 5,500 cps |
| TA | 44,000 cps |

No separation after 2 weeks at 120° F.
Example 38

| pH at 80° F. | 6.00 |
|---|---|
| viscosity | 3,400 cps |
| TA | 24,000 cps |

No separation after 2 weeks at 120° F.

EXAMPLES 39 AND 40

| ITEM | COMPONENT | 39 WT. % | 40 WT. % |
|---|---|---|---|
| 1 | polyethylene oxide (POLYOX ®) (2% active) | 20.00 | — |
| 1A | polymeric quaternary ammonium salt of hydroxyethylcellulose reacted with a lauryl dimethyl ammonium substituted epoxide (QUATRISOFT ®) (2% active) | — | 20.00 |
| 2 | ammonium lauryl sulfate (30% active) | 25.00 | 25.00 |
| 3 | cocamide MEA | 2.00 | 2.00 |
| 4 | cetyl & stearyl alcohol | 2.00 | 2.00 |
| 5 | non-volatile silicone blend | 3.00 | 3.00 |
|  | 25% SE-30 GUM 75% SF-96-50 oil |  |  |
| 6 | AROSURF ® TA-100 | 1.50 | 1.50 |
| 7 | ammonium lauryl sulfate (30% active) | 30.00 | 30.00 |
| 8 | ammonium xylene sulfonate | 2.00 | 2.00 |
| 9 | soft water | 11.65 | 11.65 |
| 10 | isopropyl myristate | 2.00 | 2.00 |
| 11 | NaOH (50%) | 0.25 | 0.25 |
| 12 | D & C orange #4 (1%) | 0.10 | 0.10 |
| 13 | fragrance | 0.35 | 0.35 |
| 14 | KATHON ® CG | 0.05 | 0.05 |
| 15 | GLYDANT ® | 0.10 | 0.10 |
|  |  | 100.00 | 100.00 |

MIXING PROCEDURE (EXAMPLES 39 and 40)

In an 800 ml beaker, combine items #1 through #3, as composition A, while stirring and heating to 155° F. In a separate 600 ml beaker, composition B, heat #4 to 180° F. and add #5 and #6. After all AROSURF ® is dissolved, add #7 and #8 and cool to 155° F. In a separate 1500 ml beaker, composition C, combine item #9 through #15 while stirring at room temperature. Add composition (A) at 155° F. to composition (C) at room temperature and mix well. Add composition (B) at 155° F. to combined composition (C) and (A) and cool to 90° F.

RESULTS (Examples 39 and 40):
Example 39

| pH as 80° F. | 5.76 |
|---|---|
| viscosity | 1400 cps |
| TA | 16,000 cps | separated at 120° F. before 2 weeks

EXAMPLE 40

Immediate separation occurred when QUATRISOFT ® was mixed with ammonium lauryl sulfate.

EXAMPLE 41 FORMULATION

| ITEM | COMPONENT | WT % |
|---|---|---|
| 1 | soft water | 25.00 |
| 2 | sodium lauryl sulfate (30% active) | 25.00 |
| 3 | cocamide MEA (VARAMIDE ® C212) | 2.00 |
| 4 | cetyl & stearyl alcohol | 2.00 |
| 5 | glycol stearate (ethylene glycol monostearate) | 1.50 |
| 6 | non-volatile silicone blend | 3.00 |
|  | 75% SF 96-50 25% SE-30 GUM |  |
| 7 | distearyldimonium chloride (AROSURF ®) | 1.50 |
| 8 | ammonium lauryl sulfate (30% active) | 27.50 |
| 9 | sodium lauryl sulfate (30% active) | 2.50 |
| 10 | soft water | 7.40 |

-continued

| | | WT. % |
|---|---|---|
| 11 | isopropyl myristate | 2.00 |
| 12 | D & C orange #4 (100%) | 0.10 |
| 13 | fragrance | 0.35 |
| 14 | methyl & chloromethyl isothiazolinone | 0.05 |
| 15 | GLYDANT ® | 0.10 |

EXAMPLE 42
FORMULATION

| ITEM | COMPONENT | WT. % |
|---|---|---|
| 1 | soft water | 25.00 |
| 2 | sodium lauryl sulfate (30% active) | 25.00 |
| 3 | cocamide MEA (VARAMIDE ® C212) | 2.00 |
| 4 | cetyl & stearyl alcohol | 2.00 |
| 5 | glyceryl stearate | 1.50 |
| 6 | dimethicone<br>75% SF 96-50<br>25% SE-30 GUM | 3.00 |
| 7 | distearyldimonmium chloride (AROSURF ®) | 1.50 |
| 8 | ammonium lauryl sulfate (30% active) | 27.50 |
| 9 | sodium lauryl sulfate (30% active) | 2.50 |
| 10 | soft water | 7.40 |
| 11 | isopropyl myristate | 2.00 |
| 12 | D & C orange #4 (100%) | 0.10 |
| 13 | fragrance | 0.35 |
| 14 | methyl & chloromethyl isothiazolinone | 0.05 |
| 15 | GLYDANT ® | 0.10 |

EXAMPLE 43
FORMULATION

| ITEM | COMPONENT | WT. % |
|---|---|---|
| 1 | soft water | 25.00 |
| 2 | sodium lauryl sulfate (30% active) | 25.00 |
| 3 | cocamide MEA/VARAMIDE ® C212 | 2.00 |
| 4 | cetyl & stearyl alcohol | 2.00 |
| 5 | stearamide MEA stearate | 1.50 |
| 6 | dimethicone<br>75% SF 96-50<br>25% SE-30 GUM | 3.00 |
| 7 | distearyldimonium chloride (AROSURF ®) | 1.50 |
| 8 | ammonium lauryl sulfate (30% active) | 27.50 |
| 9 | sodium lauryl sulfate (30% active) | 2.50 |
| 10 | soft water | 7.40 |
| 11 | isopropyl myristate | 2.00 |
| 12 | D & C orange #4 (100%) | 0.10 |
| 13 | fragrance | 0.35 |
| 14 | methyl & chloromethyl isothiazolinone | 0.05 |
| 15 | GLYDANT ® | 0.10 |

RESULTS:
Separated at room temperature overnight.

Nonionic, cross-linked ethyl acrylate polymers were substituted for the anionic CARBOPOL ® cross-linked sodium polyacrylate and it was found that about ten times the amount of nonionic polymer was needed to achieve stability for two weeks at 120° F., as shown in examples 44 and 45. In examples 44 and 45 the AROSURF ® was very difficult to blend and the compositions had visible white particles, and low viscosities. Further, the substantial increase in polymer percentage significantly reduced the lather and changed the lather feel — the lather being much more slippery than the compositions including an anionic cross-linked polymeric suspending agent.

EXAMPLES 44 AND 45
FORMULATION

| ITEM | COMPONENT | 44 WT. % | 45 WT. % |
|---|---|---|---|
| 1 | soft water | 20.0 | 20.0 |
| 2 | ethyl acrylate (ALCOGUM ® L-45) (40%) | 7.5 | 10.0 |
| 3 | sodium lauryl sulfate (30% active) | 20.0 | 20.0 |
| 4 | cocamide MEA | 2.0 | 2.0 |
| 5 | cetyl/stearyl alcohol | 2.0 | 2.0 |
| 6 | non-volatile silicone blend<br>75% SF 96-50 oil<br>25% SE-30 GUM | 3.0 | 3.0 |
| 7 | AROSURF ® TA-110 | 1.5 | 1.5 |
| 8 | sodium lauryl sulfate (30% active) | 7.5 | 7.5 |
| 9 | ammonium lauryl sulfate (30% active) | 27.5 | 27.5 |
| 10 | soft water | 6.15 | 3.65 |
| 11 | isopropyl myristate | 2.0 | 2.0 |
| 12 | NaOH 50% | 0.25 | 0.25 |
| 13 | Fragrance | 0.35 | 0.35 |
| 14 | D & C orange #4 (1%) | 0.10 | 0.10 |
| 15 | KATHON CG ® | 0.05 | 0.05 |
| 16 | GLYDANT ® | 0.10 | 0.10 |

MIXING PROCEDURE:
1. Add item #1 soft water, then add item #2 Ethyl Acrylate, begin heating to 185° F.
2. Add item #3 mix well, then add item #4 at ≈ 150° F. Mix.
3. At 160-170° F. add item #5, mix till melted, then add item #6 at 170-180° F. mix ≈ 15 minutes while shearing the silicone.
4. At 180-185° F. add AROSURF ® TA-100, increase agitation for good surface turn over, batch should appear viseous. Mix.
5. Slowly add items 8-10 over a period of 10 minutes be sure there are no solid particles.
6. At around 130-140 add item #11, mix well.
7. Add NaOH, then remainder of ingredients under 110° F.

| RESULTS (Examples 44 and 45): | 44 | 45 |
|---|---|---|
| pH 80° F. | 5.6 | 5.5 |
| viscosity | 2300 cps | 3100 cps |
| TA | 4,000 cps | 8,000 cps |

OBSERVATIONS

The AROSURF ® was very difficult to adequately blend into the "oil-phase". Batches were mixed with more than enough time at 185° F. but both contained white particles — Example #44 being the worst. The viscosity of the batches was very low (below specs.)

| 120° F. (2 wks) | 44 | 45 |
|---|---|---|
| pH at 80° F. | | 5.1 (drifted) |
| viscosity | | 3600 cps |
| TA 80° F. | | 20,000 |
| Appearance | (unstable) | ok (stable) |

Non cross-linked sodium polyacrylates (ALCOGUM ® 9710, AN10 and 296W) were used in place of the cross-linked CARBOPOL ® sodium polyacrylates and again it was found that about ten times the quantities of the non-cross-linked material was needed to achieve stability for two weeks at 120° F., as shown in Examples 46-48. The substantial increase in polymer percentage significantly reduced the lather and changed the lather feel-the lather being much more slippery than the compositions including an anionic cross-linked polymeric suspending agent. Further, two of the non cross-linked sodium polyacrylates (Example 46 and 47) were not stable for 2 weeks at 120° F.

EXAMPLES 46–48

| ITEM | FORMULATION COMPONENT | 46 WT. % | 47 WT. % | 48 WT. % |
|---|---|---|---|---|
| 1 | sodium lauryl sulfate (30% active) | 27.5 | 27.5 | 27.5 |
| 2 | ALCOGUM ® 9710 (12% active) | 25.0 | — | — |
| 3 | ALCOGUM ® AN10 (10% active) | — | 30.0 | — |
| 4 | ALCOGUM ® 296W (15% active) | — | — | 20.0 |
| 5 | cocamide MEA | 2.0 | 2.0 | 2.0 |
| 6 | cetyl/stearyl alcohol | 2.0 | 2.0 | 2.0 |
| 7 | non-volatile silicone blend 75% SF 96-50 25% SE-30 GUM | 3.0 | 3.0 | 3.0 |
| 8 | AROSURF ® TA-100 | 1.5 | 1.5 | 1.5 |
| 9 | ammonium lauryl sulfate (30% active) | 27.5 | 27.5 | 27.5 |
| 10 | soft water | 6.9 | 1.9 | 11.9 |
| 11 | isopropyl myristate | 2.0 | 2.0 | 2.0 |
| 12 | FD & C orange #4 (1%) | 0.1 | 0.1 | 0.1 |
| 13 | fragrance | 0.35 | 0.35 | 0.35 |
| 14 | KATHON ® | 0.05 | 0.05 | 0.05 |
| 15 | GLYDANT ® | 0.10 | 0.10 | 0.10 |
| 16 | ammonium xylene sulfonate | 2.0 | 2.0 | 2.0 |

OBSERVATIONS

The "oil-phases" were all extremely thick. Upon dilution, the batches remained fairly viscous. An additional 2% ammonium xylene sulfonate had to be added to adequately thin the batches down.

RESULTS:

|  | 46 | 47 | 48 |
|---|---|---|---|
| pH at 80° F. | 8.5 | 6.8 | 6.9 |
| viscosity | 10,000 cps | 17,000 cps | 5000 cps |
| TA | 80,000 cps | 120,000 cps | 36,000 cps |

What is claimed is:

1. A hair conditioning shampoo composition comprising an emulsion of water; about .5 to about 65 percent by weight of an anionic cleaning surfactant; from about 0.1 to about 20 percent by weight of a cationic di-long chain alkyl quaternary nitrogen-containing conditioning agent, wherein the long alkyl chains bonded to the nitrogen atom have from about 12 to about 22 carbon atoms per alkyl chain; from about 0.5 to about 10 weight percent of a long chain fatty alcohol having about 8 to about 32 carbons in the long chain; from about 0.5 to about 10 weight percent of a non-volatile silicone; and about 0.1 to about 5% of an anionic cross-linked polymeric suspending agent.

2. The hair conditioning shampoo composition according to claim 1 wherein said non-volatile silicone is present in an amount of about 1.5 to about 5 percent by weight of said composition.

3. The hair conditioning shampoo composition according to claim 1 wherein said quaternary nitrogen-containing conditioning agent is a quaternary ammonium salt containing two alkyl radicals having a carbon chain length from about 12 to about 18 carbon atoms per radical.

4. The hair conditioning shampoo composition according to claim 1 wherein said quaternary nitrogen-containing conditioning agent is present at about 1 percent to about 3 percent by weight of the composition.

5. The hair conditioning shampoo composition according to claim 1 wherein said long chain fatty alcohol is present in an amount of about 2 to about 5 weight percent of said composition.

6. The composition of claim 1 wherein the non-volatile silicone has a viscosity at 25° C. of at least 5 centistokes and a boiling point at 760 mm Hg pressure and 25° C. of at least 250° C.

7. The composition of claim 1 wherein the polymeric suspending agent is a cross-linked acrylic resin.

8. The composition of claim 7 wherein the cross-linked resin is polyacrylic acid or a metal salt of polyacrylic acid and is present in an amount of about 0.1% to about 3% by weight of the composition.

9. The hair conditioning composition according to claim 1 wherein said long chain fatty alcohol is selected from the group consisting of cetyl alcohol, stearyl alcohol and mixtures thereof.

10. The hair conditioning composition according to claim 1 wherein said quaternary nitrogen-containing conditioning agent is selected from the group consisting of (a) compounds having two long carbon chains and two identical or different short chain alkyl groups containing one to four carbon atoms bonded to the quaternary nitrogen atom, (b) compounds having two long carbon chains, one benzyl group and one short chain alkyl group having one to four carbon atoms bonded to the quaternary nitrogen atom, and (c) compounds having two long carbon chains, one hydrogen atom and one short chain alkyl group having one to four carbon atoms bonded to the quaternary nitrogen atom.

11. In a hair conditioning shampoo composition containing water, an anionic cleaning surfactant, a fatty alcohol, a non-volatile silicone and a quaternary nitrogen-containing conditioning agent, the improvement comprising the conditioning agent having only two long chain alkyl groups bonded to the quaternary nitrogen atom, and an anionic polymeric suspending agent, in an amount of about 0.1% to about 5% by weight of the composition.

12. A method of shampooing and conditioning hair which comprises applying to said hair the composition of claim 1.

13. A method of shampooing and conditioning hair simultaneously which comprises applying to said hair the composition of claim 11.

14. A method of manufacturing the conditioning shampoo composition of claim 1 comprising:
heating a mixture of water, an anionic, polymeric suspending agent, and an anionic surfactant to a temperature above the melting point of the fatty alcohol;
adding the fatty alcohol to said heated water until said alcohol is completely melted to form an anionic alcohol solution;
adding the non-volatile silicone to said alcohol solution to form a two-phase composition;
vigorously agitating the two-phase composition to break up the silicone into droplets;
adding the di-long chain alkyl quaternary nitrogen-containing conditioning agent before or after said vigorous agitation while maintaining the temperature of the two phase composition at or above the melting point of said conditioning agent to form a stable emulsion having a viscosity of about 5,000 centipoises to about 20,000 centipoises.

15. The method of claim 14 further including adding 1-20% of the water and a proportionate quantity of the anionic surfactant to the composition after said vigorous agitation.

16. The method of claim 14 wherein said non-volatile silicone is present in an amount of about 1.5 to about 5 percent by weight of said composition.

17. The method of claim 14 wherein said quaternary nitrogen-containing conditioning agent is a quaternary ammonium salt containing two alkyl radicals having a carbon chain length from about 12 to about 18 carbon atoms per radical.

18. The method of claim 14 wherein said quaternary nitrogen-containing conditioning agent is present at about 2 to about 3 percent by weight of the composition.

19. The method of claim 14 wherein said long chain fatty alcohol is present in an amount of about 2 to about 5 weight percent of said composition.

20. The method of claim 14 wherein the non-volatile silicone has a viscosity at 25° C. of at least 5 centistokes and a boiling point at 760 mm Hg pressure and 25° C. of at least 250° C.

21. The method of claim 14 wherein the polymeric suspending agent is a cross-linked acrylic resin.

22. The method of claim 21 wherein the cross-linked resin is polyacrylic acid or a metal salt of polyacrylic acid and is present in an amount of about 0.1% to about 3% by weight of the composition.

23. The method of claim 14 wherein said long chain fatty alcohol is selected from the group consisting of cetyl alcohol, stearyl alcohol and mixtures thereof.

24. A hair conditioning shampoo composition comprising an emulsion of water; about 5 to about 65 percent by weight of an anionic cleaning surfactant; from about 0.1 to about 20 percent by weight of a cationic di-long chain alkyl quaternary nitrogen-containing conditioning agent, wherein the long alkyl chains bonded to the nitrogen atom have from about 12 to about 22 carbon atoms per alkyl chain; from about 0.5 to about 10 weight percent of a long chain fatty alcohol having about 8 to about 32 carbons in the long chain; from about 0.5 to about 10 weight percent of a non-volatile silicone; and about 0.1 to about 5% of guar gum.

25. The hair conditioning shampoo composition according to claim 24 wherein said quaternary nitrogen-containing conditioning agent is a quaternary ammonium salt containing two alkyl radicals having a carbon chain length from about 12 to about 18 carbon atoms per radical.

* * * * *

UNITED STATES PATENT AND TRADEMARK OFFICE
CERTIFICATE OF CORRECTION

PATENT NO. : 5,034,218
DATED : July 23, 1991
INVENTOR(S) : LANE A. DUVEL

It is certified that error appears in the above—identified patent and that said Letters Patent is hereby corrected as shown below:

Column 23, before "EXAMPLE 42", insert
-- RESULTS:
   Separated at room temperature overnight. --; and Column 23, before "EXAMPLE 43", insert
-- RESULTS:
   Separated at room temperature overnight. --.

Signed and Sealed this

Seventh Day of September, 1993

Attest:

BRUCE LEHMAN

Attesting Officer  Commissioner of Patents and Trademarks